(12) United States Patent
Portney et al.

(10) Patent No.: US 9,510,939 B2
(45) Date of Patent: Dec. 6, 2016

(54) MULTI-MODE OPERATING OPTIC FOR PRESBYOPIA CORRECTION

(71) Applicants: Valdemar Portney, Newport Coast, CA (US); Nathaniel G. Portney, San Diego, CA (US)

(72) Inventors: Valdemar Portney, Newport Coast, CA (US); Nathaniel G. Portney, San Diego, CA (US)

( * ) Notice: Subject to any disclaimer, the term of this patent is extended or adjusted under 35 U.S.C. 154(b) by 0 days.

(21) Appl. No.: 14/637,407

(22) Filed: Mar. 4, 2015

(65) Prior Publication Data

US 2015/0173890 A1    Jun. 25, 2015

Related U.S. Application Data

(63) Continuation-in-part of application No. 14/039,322, filed on Sep. 27, 2013.

(60) Provisional application No. 61/949,111, filed on Mar. 6, 2014, provisional application No. 61/711,092, filed on Oct. 8, 2012.

(51) Int. Cl.
*A61F 2/16*    (2006.01)

(52) U.S. Cl.
CPC ........... *A61F 2/1618* (2013.01); *A61F 2/1601* (2015.04); *A61F 2/1627* (2013.01); *A61F 2/1654* (2013.01)

(58) Field of Classification Search
CPC .... A61F 2/1601; A61F 2/1618; A61F 2/1627; A61F 2/1654; A61F 2/1635; A61F 2/1648; A61F 2250/0003; A61F 2250/0004; A61F 2250/0009; A61F 2250/0013; A61F 2250/0053; A61F 2250/0091
See application file for complete search history.

(56) References Cited

U.S. PATENT DOCUMENTS

| | | | | |
|---|---|---|---|---|
| 4,585,457 A | * | 4/1986 | Kalb | A61F 2/1616 623/6.13 |
| 4,657,546 A | * | 4/1987 | Shearing | A61F 2/1648 623/6.21 |
| 4,685,921 A | * | 8/1987 | Peyman | A61F 2/1613 623/6.13 |
| 4,731,078 A | * | 3/1988 | Stoy | A61F 2/1648 623/6.13 |
| 4,786,445 A | | 11/1988 | Portnoy et al. | |
| 4,932,966 A | * | 6/1990 | Christie | A61F 2/1613 623/6.13 |

(Continued)

*Primary Examiner* — Paul Prebilic
(74) *Attorney, Agent, or Firm* — Hackler Daghighian Martino & Novak (57) ABSTRACT

A switchable intraocular lens assembly includes an optic body having a guiding surface, a holding chamber, a blocking channel, and a laser accessible cavity at a portion of the blocking channel. An elastic film is disposed over the guiding surface, wherein the elastic film is sealed at or near the guiding surface periphery forming a transparent chamber between the guiding surface and the elastic film. A laser flowable blocking element has an enlarged head connected to an extension portion, where a length of the extension portion is more than a distance along the blocking channel from the blocking channel opening to the fluidic connection of the transparent chamber. The extension portion of the laser flowable blocking element is disposed inside the blocking channel. An optical fluid is disposed within the holding chamber under a pressure greater or lesser in comparison to a pressure in the transparent chamber.

26 Claims, 5 Drawing Sheets

(56) References Cited

U.S. PATENT DOCUMENTS

| | | | |
|---|---|---|---|
| 5,770,125 A | 6/1998 | O'Connor et al. | |
| 6,730,123 B1* | 5/2004 | Klopotek | A61F 2/1613 |
| | | | 623/6.22 |
| 7,122,053 B2* | 10/2006 | Esch | A61F 2/1616 |
| | | | 623/6.13 |
| 2003/0060878 A1* | 3/2003 | Shadduck | A61F 2/1613 |
| | | | 623/6.13 |
| 2003/0149480 A1* | 8/2003 | Shadduck | A61F 2/1648 |
| | | | 623/6.41 |
| 2004/0190153 A1* | 9/2004 | Esch | A61F 2/16 |
| | | | 359/666 |
| 2008/0161914 A1* | 7/2008 | Brady | A61F 2/1635 |
| | | | 623/6.46 |
| 2011/0118834 A1* | 5/2011 | Lo | A61F 2/1635 |
| | | | 351/159.68 |
| 2014/0085726 A1 | 3/2014 | Portney | |

\* cited by examiner

MULTI-MODE OPERATING OPTIC FOR PRESBYOPIA CORRECTION

CROSS-REFERENCE TO RELATED APPLICATIONS

The present application claims priority from U.S. Provisional Patent application Ser. No. 61/949,111 filed Mar. 6, 2014. The present application is also a continuation-in-part of application Ser. No. 14/039,322 filed on Sep. 27, 2013, which itself claimed priority to provisional application 61/711,092 filed on Oct. 8, 2012. These applications are to be incorporated in their entirety into the present application with these references.

DESCRIPTION

Field of the Invention

The present invention relates generally to a fluidic lens that changes its operating mode in terms of imaging at its focus portion upon remotely affecting a surface shape of the fluidic lens. More particularly, the present invention relates to a blocking mechanism that maintains shape of a fluidic lens constant in order to maintain the lens in specific mode of operation. The blocking mechanism is remotely unblocked by a laser beam action to change the fluidic lens to a different mode of operation with different shape of a fluidic lens surface.

Background of the Invention

U.S. patent application Ser. No. 14/039,322 introduced a remote conversion of the switchable implant from multifocal to monofocal mode of operation without a need for an invasive surgery for the lens exchange. Here we will introduce a blocking mechanism applicable to any fluidic lens including a switchable implant to allow a change in mode of operation, for instance between multifocal and monofocal mode of operations or between monofocal and accommodating mode of operations of different focus positions due to optical power change. The U.S. patent application Ser. No. 14/039,322 is to be incorporated in its entirety into this application with this reference.

An ophthalmic implant in the present invention is defined as a fluidic lens suitable for placement inside the eye such as aphakic and phakic intraocular lenses or implants placed in posterior or anterior eye chamber and also included are artificial corneas and corneal implants or inlay. The fluidic lens per the present invention consists of two fluid chambers, one, so called transparent chamber of the implant, is the chamber contributing to image forming performance of the fluidic lens and another, so called holding chamber of the implant, is for a fluid balance for fluid communication with the transparent chamber. The fluid communication between transparent and holding chambers is severed in one mode of operation of the fluidic lens and opened in another mode of operation. For detailed explanation of the lens of the present invention, the ophthalmic application for presbyopia correction by refractive-diffractive switchable (RDS) intraocular implant is disclosed in U.S. Patent Application Publication Number 2014/0085726.

There is a significant effort to develop a lens for presbyopia correction in a form of multifocal refractive or multifocal diffractive lenses that produce multiple foci for far and near vision. There is also significant effort to develop an accommodating lens that changes eye optical power between far and near foci under the action of ciliary muscles. Each of these platforms (multifocal and accommodating one) caries own challenges: (1) reduced image quality due to multiple foci in a multifocal optic, i.e. there is an issue with safety of a multifocal optic and (2) uncertainty with accommodating implant ability to change ocular optical power between far and near foci in sync with ciliary muscle relaxation and contraction, i.e. efficacy of an accommodating optic. The fundamental issue is that all current lenses for presbyopia correction manifest single mode of operation, i.e. a lens is implanted in multifocal mode of operation that can't be changed without physically removing the lens from the eye for its replacement with monofocal lens or a lens is implanted in the eye in accommodating dynamic mode of operation with a hope that it will act accordingly to ciliary muscles contraction and relaxation which commonly is not the case with present designs.

The present invention describes optic for presbyopia correction that includes multi-mode operation that a surgeon can remotely switch at certain conditions. For instance, in case of multifocal multi-mode optic, the remote switching from multifocal to monofocal mode of operation occurs if the patient can't tolerate multifocal image quality, i.e. too low image contrast or experiencing significant photic phenomena such as halos or glare. In case of accommodating multi-mode optic, the remote switching from monofocal to accommodating mode of operation occurs in the condition of stability with post-operative healing as well as lens position, shape or other characteristics that had been established as necessary for effective accommodating performance of switching between far and near foci in sync with ciliary muscles relaxation and contraction.

Multi-mode optic is a fluidic lens of any configuration that includes two fluid chambers (transparent and holding chambers) with blocking mechanism between them that severs fluid communication between the fluid chambers in one mode of operation and allows fluid communication between the fluid chambers with remote unblocking the blocking mechanism in another mode of operation. Generally, the lens also can be a gas lens. The present invention discloses a configuration of the blocking mechanism that prevents fluid communication between the fluid chambers and an unblocking procedure for unblocking to then allow fluid communication between the fluid chambers.

The disclosed blocking mechanism has been applied to the refractive-diffractive switchable (RDS) lens disclosed in the U.S. patent application Ser. No. 13/626,118 (Publication Number 2014/0085726). The content of the U.S. patent application Ser. No. 13/626,118 is included in the present application in its entirety with this reference. RDS lens includes optical substrate with diffraction (or refractive) surface called guiding surface, elastic film in contact with the guiding surface, optical fluid called matching fluid that fills a space between the film and guiding surface and called transparent chamber and a channel to transfer the matching fluid in and out of the transparent chamber to a holding chamber. An operation of a RDS optic relies on the ability of matching fluid to optically mask the guiding surface resulting in light interaction with a matching fluid surface shaped by the elastic film instead of the guiding surface itself. A shape of the matching fluid surface is controlled by elastic film shape. By changing a shape of the elastic film one can control a shape of the matching fluid surface thus controlling an image position or quality of the corresponding RDS lens. Elastic film is usually of uniform thickness and, therefore, its contribution to the optical performance is negligible though it might be non-uniform to add additional optical characteristic such as aspherization, for instance. Therefore, generally a discussion of RDS performance in terms of transparent chamber shape references to the shape of the external surface of the elastic film, i.e. the surface of the film external to the guiding surface of the RDS lens.

SUMMARY OF THE INVENTION

A multi-mode operating lens according to the present invention incorporates (1) a fluidic lens with at least two fluid chambers, transparent chamber effecting imaging character of the lens and holding chamber for fluid communication with transparent chamber in order to change transparent chamber shape and, a result, fluidic lens imaging characteristic, (2) blocking mechanism to sever fluid communication between the transparent and holding chambers for fixing fluidic lens shape for one imagine performance condition called mode of operation and (3) a procedure of remote unblocking the blocking mechanism by a laser beam to open fluid communication between transparent and holding chambers in order to change the fluidic lens to a different imaging performance condition, i.e. a different mode of operation.

Blocking mechanism includes: (1) a blocking channel separating transparent and holding chambers of the fluidic lens, (2) blocking element made of a flowable material, i.e. a material that melts under a laser beam radiation for fluid like flow. The blocking element is placed into the blocking channel to sever a fluid communication between the transparent and holding chambers, (3) cavity within the blocking channel which is filled by flowable blocking element material melted under the laser beam radiation in unblocking procedure. The expansion of the blocking element material within the cavity pulls out the portion of the blocking element that severs fluid communication between transparent and holding chambers thus opening fluid communication between the chambers.

The process of filling a capsule within the blocking channel by a flowable material under a laser beam material takes a cue from the process known as laser staking used with multi-piece intra-ocular lenses in 1990s for attaching fixation members to the optic body. The laser staking process of the fixation member attachment to the optic body by the laser beam was described in the U.S. Pat. Nos. 4,786,445 and 5,770,125. The process involved melting the fixation member portion into flowable (fluid like) material to fill the space within the optic body for attaching the fixation member to the optic body.

Blocking mechanism per the present invention has multiple applications, for instance it can be included in fluidic lens to change its optical power in specific steps. The fluid in holding chamber can be transferred to transparent chamber of the fluidic lens of certain power with unblocking the blocking mechanism in order to increase the curvature of the lens membrane thus increasing the power of the lens in case of convex surface. This occurs if the pressure in the holding chamber is higher the pressure in the transparent chamber. The curvature at the transparent chamber can be reduced upon unblocking the blocking mechanism if the pressure in the chamber is higher the pressure in the holding chamber.

There are many other option of fluidic lens configurations and one of them, Refractive-diffractive switchable lens, is used in the present invention to explain the blocking mechanism for conversion of a fluidic lens into multi-mode operating lens where unblocking the blocking mechanism switches the lens from one refractive state or image forming condition into another refractive state or image forming condition (optical power change, multifocality change, etc.).

The blocking mechanism allows for a conversion of a RDS lens into multi-mode RDS lens per present invention for its mode switching from multifocal to monofocal mode of operation in case of multifocal RDS implant in order to manage its safety issue or from monofocal to accommodating mode of operation in case of accommodating RDS lens in order to manage its efficacy issue.

A multifocal RDS lens includes multifocal guiding surface at its optical substrate where "multifocal" means a formation of several foci by the lens. Multifocal guiding surface might be diffractive type that forms images by constrictive interference of lights at specific foci or refractive type where images are formed at multiple foci by refraction of light at lens zones of different powers or by a combination of diffractive and diffractive areas of the guiding surface. Matching fluid covers the guiding surface and exterior matching fluid shape is maintained by the elastic thin film. The chamber formed between the guiding surface and the film is called transparent chamber. A channel connects transparent chamber with a holding chamber which can be within the lens optic or outside lens optic. The holding chamber holds a balance of fluid if it is to move from the transparent chamber or into the transparent chamber with opening fluid communication between them. As the transparent chamber is filled, the elastic film is taking resting state to form a single focus (monofocal) refractive surface by its external surface resulting in the multifocal RDS lens to become a monofocal refractive lens. As the fluid is largely removed from the transparent chamber, the film being a deformable element, is converted into active state by largely taking a shape of the multifocal guiding surface and the RDS lens to manifest equivalement multifocal imaging performance.

A multifocal multi-mode RDS lens is implanted in the eye in its multifocal mode of operation, i.e. the elastic film is in active state of largely taking the multifocal shape of the guiding surface. No image quality adjustment is required if a patient accepts the resulted multifocal vision provided by the lens. A multi-mode operating characteristic of the multifocal RDS lens comes into play only if a patient is substantially unhappy with the vision outcome. If required, the fluid communication between transparent and holding chambers is remotely opened for the fluid flow from holding to transparent chamber and converting the elastic film from active to resting state resulting in monofocal mode of operation of the lens. Monofocal mode of operation reduces or eliminates a light flow to near focus thus improving far vision quality by this corresponding virtual lens exchange without engaging in present days highly invasive procedure of opening the eye and the physically exchanging the multifocal lens for a monofocal lens. The process is called mode switching. Note, "near" vision in the present invention is used in a general term corresponding to a light not allocated to far vision thus may including also an intermediate focus in addition to the actual near focus where "intermediate" usually references to viewing distance between 4 meter and 0.5 meter form he eye, and "near" usually references to viewing distance of 0.5 meter and closer thus leaving far vision to distance of 4 meter and beyond.

An accommodating multi-mode RDS lens includes monofocal diffractive guiding surface usually for near focus. Similar to multifocal RDS lens above, matching fluid covers the guiding surface and matching fluid shape is maintained by the elastic thin film. The chamber formed between the guiding surface and the film, i.e. transparent chamber, is connected with a holding chamber which can be within the lens optic or outside lens optic. The holding chamber holds a balance of fluid if it is to move from or to transparent chamber for switching between far and near foci when in accommodating mode of operation. As the transparent chamber is filled, the elastic film is taking resting state to form a single focus (monofocal) refractive surface by the external surface of the elastic film resulting in monofocal refractive lens usually for far vision. As the fluid is largely removed from the transparent chamber, the film being a deformable element, is converted into active state by largely taking a shape of the guiding monofocal diffractive surface and the lens manifests equivalement monofocal performance for near focus. Guiding diffractive surface may include intermediate focus in addition to near focus. In general, lens with film in resting state may manifest power for near and in active state, a power for far with or without intermediate focus added either in resting or actives state but for practical reason the resting state of the film is allocated to far focus by the lens.

Accommodating multi-mode RDS lens is implanted in monofocal mode of operation defined as static monofocal lens with fixed optical power, usually for far vision. This is to insure that the conditions for effective performance in accommodating mode of operation can be verified before the lens is converted into accommodating mode of operation, i.e. into a dynamic lens with variable optical power between far and near foci that switches in between under the action of ciliary muscles relaxation and contraction. Thus, as the conditions for affective accommodating performance are verified, a communication between transparent and holding chambers are remotely open to enable fluid communication between transparent and holding chambers. Accommodating lens is designed to change between far and near foci under the actions of ciliary muscles that forces the fluid transfer between transparent and holding chambers, i.e. between resting state of the elastic film for the lens far power and active state of the elastic film that largely follows the shape of the guiding surface for the lens near focus. Both, blocking mechanism in multifocal and accommodating multi-mode RDS lenses are similar.

A blocking element of the blocking mechanism is made, for instance, a polypropylene fiber. The fiber can be made of any material that can be melted by an appropriate laser beam and, as a result, unblocking the fluids communication between the transparent and holding chambers for the fluid to flow between them. The blocking element is placed in so called blocking channel to block fluid communication between transparent and holding chambers. The blocking channel includes a cavity where melted by the laser beam portion of the blocking element material flow into during unblocking procedure thus pulling the blocking element along the blocking channel towards the cavity and opening the flow communication between transparent and holding chambers. The unblocking procedure involves blocking element material melting by, for instance, Nd:YAG laser beam or a different laser. It is generally desirable but not necessary that the wavelength of the laser beam is such that it does not melt the optic material itself but only the blocking fiber material due to a difference in radiation absorptions. Polypropylene fiber, for instance, is readily available and commonly made in blue color thus easily absorbing near infrared laser beam emitted by Nd:YAG laser which is also readily available in ophthalmic practices for posterior capsulotomy procedures.

It is also possible to reverse the mode switching between the modes of operation from monofocal mode of operation back to multifocal mode of operation by including additional blocking mechanisms with correspond additional holding chambers. In this case the fluid pressure in this additional holding chamber is lower the fluid pressure at the transparent chamber and by unblocking the fluid communication between the chambers forces the fluid to flow from the transparent to this additional holding chamber. This forces the elastic film to take shape of the multifocal guiding surfaced again to largely restoring multifocal performance. In generally, it may be multiple blocking mechanisms each with corresponding holding chamber for multiple alteration between the modes of operation, monofocal and multifocal, optical powers.

Blocking mechanism is included in accommodating multi-mode operating optic for its initial implantation in the monofocal mode of operation usually for far vision. It may take few months for the eye to heal and during this time the lens performs as a conventional monofocal lens. Optical and ultrasound microscopy allows testing for optic and supporting member positions and configurations to determine if they are in desirable states for effective interaction with the ciliary muscle or any other ocular element responsible for accommodation effect, crystalline lens capsule, for instance. There is advantage to apply the blocking mechanism for multi-mode operation of the accommodating lens described in the U.S. Patent Application Publication Number 2014/0085726 entitled "Refractive Diffractive Switchable Optical Element", FIGS. 4-7. The described accommodating optic switches between far and near foci with slight haptic (optic supporting member) angulation change. It is also possible to physically adjust the lens or haptics position by a probe through a very small eye opening for a desirable configuration before switching the lens to the accommodating mode of operation.

In one embodiment disclosed herein a switchable intraocular lens assembly is configured for implantation in an eye. An optic body defines a body thickness between a first surface opposite a second surface. The optic body includes: at least two supporting members extending from a periphery of the optic body where the at least two supporting members are configured for implant fixation inside the eye; a guiding lens formed in the front surface; at least one fluid transport trench formed in the optic body along a portion of the guiding lens and front surface; a first through hole disposed through the body thickness between the first and second surfaces, wherein the first through hole is disposed outside a guiding lens periphery, and wherein the first through hole is in fluidic communication with the at least one fluid transport trench; a holding chamber formed in the body thickness along the first surface and located outside the guiding lens periphery; a second through hole disposed through the body thickness between the first and second surfaces, the second through hole in fluidic communication with the holding chamber; a blocking channel formed in the body thickness of the optic body, the blocking channel in fluidic communication with the at least one fluid transport trench and the holding chamber, the blocking channel having a blocking channel opening in the optic body at a proximal end of the blocking channel, where the holding chamber is connected at a distal end of the blocking channel, wherein the at least one fluid transport trench is connected to the blocking channel between the proximal and distal ends of the blocking channel; and a third through hole disposed through the body thickness between the first and second surfaces, the third through hole passing through a portion of the blocking channel located between the blocking channel opening and the connection of the at least one fluid transport trench to the blocking channel. An elastic film is disposed over the guiding lens, the first through hole, the second through hole and the holding chamber, wherein the elastic film is sealed at or near the guiding lens periphery along the first surface forming a transparent chamber between the guiding lens and the elastic film, and wherein the elastic film is sealed at a periphery of the holding chamber along the first surface forming an enclosed cavity of the holding chamber. A laser flowable blocking element has an enlarged head connected to an extension portion, where a length of the extension portion is more than a distance along the blocking channel from the blocking channel opening to the connection of the at least one fluid transport trench, wherein the extension portion of the laser flowable blocking element is disposed inside the blocking channel. A first seal seals the first through hole along the second surface. A second seal seals the second through hole along the second surface. An optical fluid disposed within the holding chamber.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 9 demonstrates a front view of accommodating multi-mode operating RDS lens per present invention where the principle of accommodation of the intra-ocular lens for aphakia described in the U.S. Patent Application 2014/0085726, FIGS. 4-7, is applied, i.e. a change in optical power between far and near foci of the corresponding accommodating RDS lens occurs with small change in haptics' (supporting members) angulation;

DETAILED DESCRIPTION OF THE PREFERRED EMBODIMENTS

Figure 1:
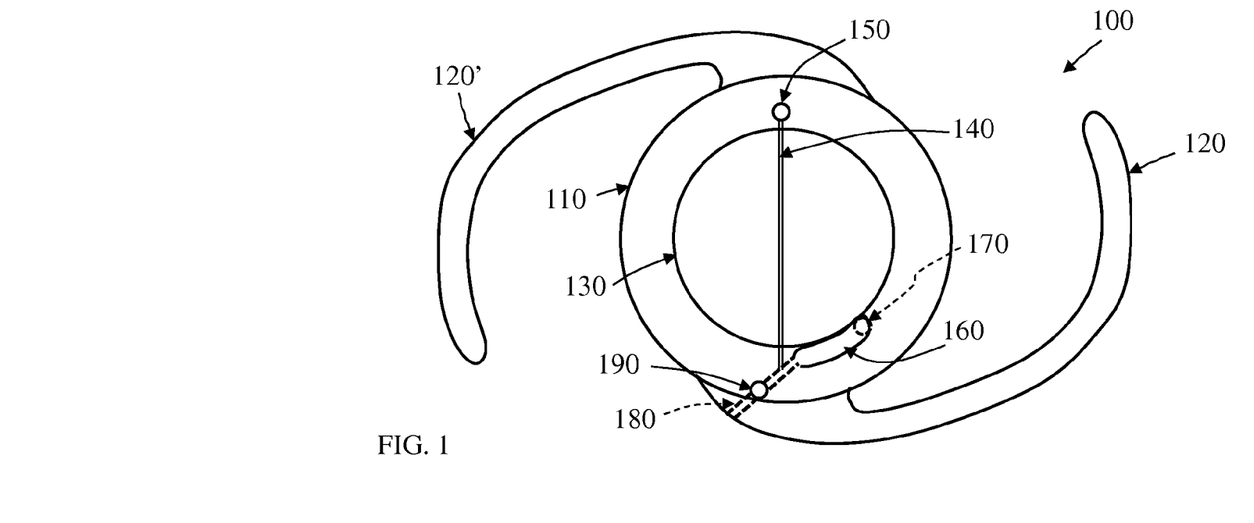
FIG. 1 shows a front view of multifocal two-mode operating RDS lens with exposed guiding surface prior to elastic film bonding and also prior to blocking element installation for blocking mechanism assembly. The RDS lens is used as the way of example to explain the blocking mechanism as well as the example of multi-mode operating RDS lens configuration.

FIG. 1 demonstrates blocking mechanism according to the present invention for switching between modes of operation on the example of refractive-diffractive switchable intra-ocular implant 100 (RDS IOL) consisting of the optic body 110 and two supporting members (haptics) 120 and 120' for the implant fixation inside the eye. The implant 100 consists of single lens optic body but an optic body may consists of several lenses. There is optical diffractive surface 130 on one of front and back surface of the optic body 110. Diffractive surface 130 is multifocal diffractive surface in a switchable multifocal implant. The diffractive surface 130 is guiding surface of RDS implant though a guiding surface might be a refractive multifocal in other embodiments. The reference to guiding surface is used to describe both types of diffractive surface and refractive surface.

Trench channel 140 (groove/channel) passes across the diffractive surface to transport fluid to and from the space adjacent to the guiding surface 130. This type of channel is the easiest channel to manufacture though a channel may also pass within the optic body 110 itself and the reference to channel is used throughout this application to describe both channel types. There is a connecting through hole 150 at the optic periphery to help with fluid introduction into the channel 140. The channel 140 connects the space adjacent to diffractive surface for forming transparent chamber with the holding chamber 160. Generally speaking, a holding chamber can be any chamber to maintain a balance of fluid and located largely outside the optical zone of an implant where optical zone is an image forming portion of an implant optical body. The holding chamber 160 includes holding through hole 170 to allow fluid to fill the space adjacent to the guiding surface 130 and well as the holding chamber 170.

Blocking mechanism per the present invention includes blocking channel 180 connecting the holding chamber 160 and channel 140 by its section. The blocking channel 180 also includes a cavity, in this case in a form of blocking through hole 190.

Figure 2:
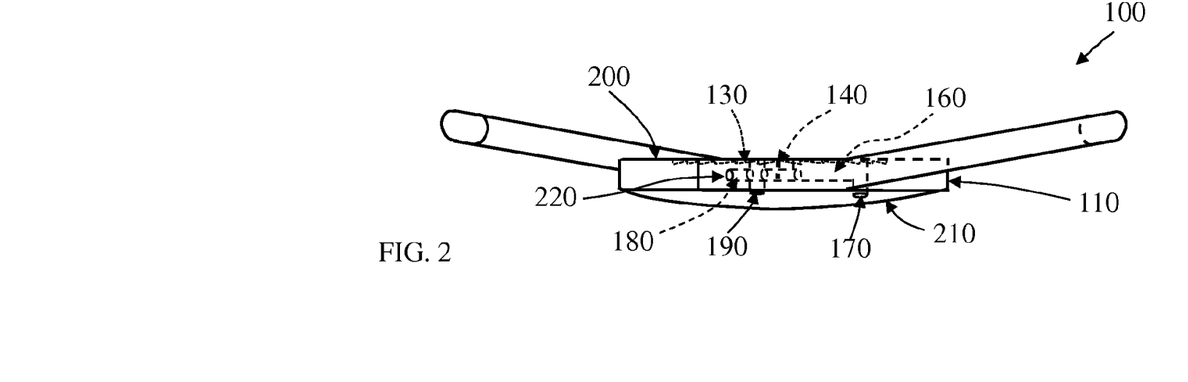
FIG. 2 demonstrates a side view of not fully assembled RDS lens of the FIG. 1.

FIG. 2 demonstrates a side view of the implant 100 shown on the FIG. 1. It shows diffractive surface 130 on front surface 200 of the optical body 110. A diffractive surface is characterized by grooves periodicity and height with the grooves placed over virtual base surface which can be flat, curved and aspheric. A guiding surface can be also placed on back surface 210. The channel 140 passes across the diffractive surface and intersects the blocking channel 180 connected with the holding chamber 160 which also includes holding through hole 170. The FIG. 2 also shows a blocking though hole 190 that crosses the blocking channel 180 with an opening at least at one of anterior and posterior surfaces. In general a cavity at the blocking channel may be inside the optic body. It is also shown blocking channel opening 220 of the blocking channel 180 at the peripheral edge of the optic body 110 though the opening might be at any part of the optic body periphery including anterior or posterior surface.

Figure 3:
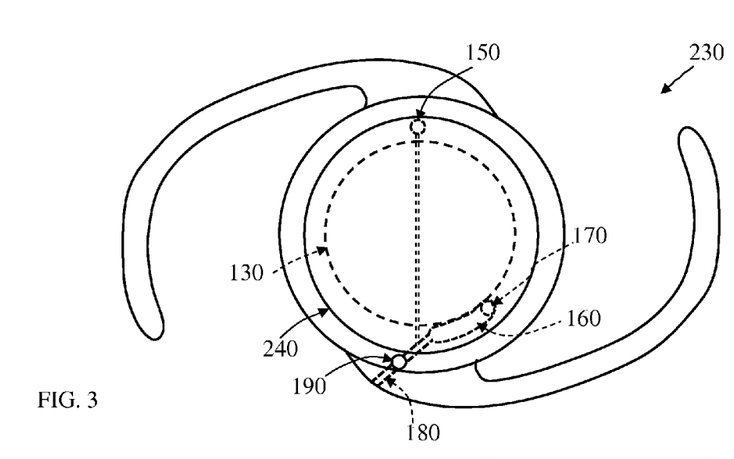
FIG. 3 demonstrates a front view of the lens on FIG. 1 with the elastic film bonded over the guiding surface.

FIG. 3 shows front view of the implant 100 of the FIG. 1 with addition of elastic film 240 placed over the guiding surface 130 together forming implant 230. The elastic film 240 is bonded to surface outside the guiding surface 130 to be over the connecting through hole 150 and holding chamber 160 to form enclosed cavity of the holding chamber and also over the guiding surface 130, to form so called transparent chamber. The film 240 is sized to leave the blocking though hole 190 connected with the blocking channel 180 uncovered by the film.

Figure 4:
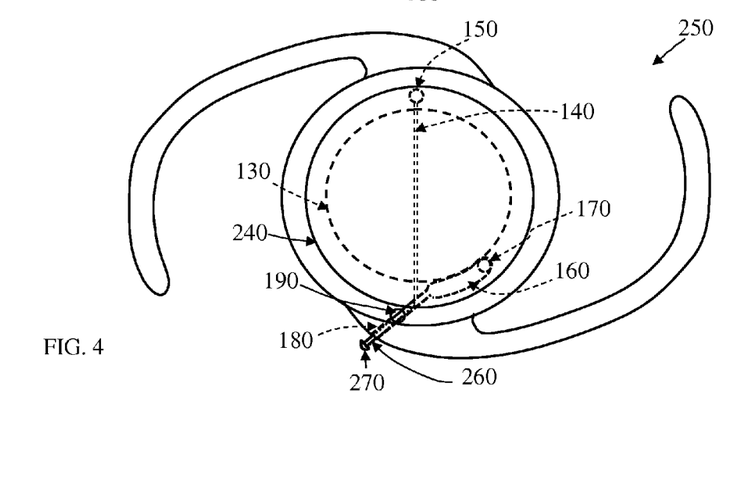
FIG. 4 illustrates a front view of the lens of the FIG. 3 with the blocking element placed into the blocking channel in its initial position with fluid communication between the transparent and holding chambers is still maintained.

FIG. 4 illustrates front view of the implant 230 of FIG. 3 with the introduction of a blocking element 260 into the blocking channel 180 forming together the implant 250. The blocking element 260 can be made of polypropylene material which was commonly used as a fixation member in three-piece intra-ocular lenses or any other biologically compatible material that can melt into flowable state under a laser radiation. The blocking element 260 is inserted into the blocking channel 180 reaching just before the intersection between the channel 140 and blocking channel 180 thus leaving the channel 140 communication with the holding chamber 160 opened but blocking a communication between the blocking through hole 190 at the blocking channel 180 and the channel 140. The blocking element 260 is another member of the blocking mechanism. The blocking element 260 is shown as extending out (extension portion) of the blocking chamber 180 by the certain length and having an expansion at its end called blocking element head (cap) 270. A diameter of the blocking element head 270 is larger the internal diameter of the blocking channel 180.

Optical fluid is injected into one of the connecting through hole 150 and holding through hole 170 enough to fill the space between the elastic film 240 and diffractive surface 130 through the channel 140 to form transparent chamber as well as filling the holding chamber 160. Note, the film in the resting state can be radially stretched as the resting state characterized by the refractive optical property of the exterior surface of the elastic film as described in the U.S. patent application Ser. No. 14/039,322 with no elastic film conformance to the guiding surface shape. Upon the matching optical fluid filling the transparent and holding chambers, the openings of the connecting through hole 150 and holding through hole 170 at the posterior surface are closed with a glue or cork (a seal) made of a biocompatible material to seal the matching fluid inside the transparent and holding chambers.

Figure 5:
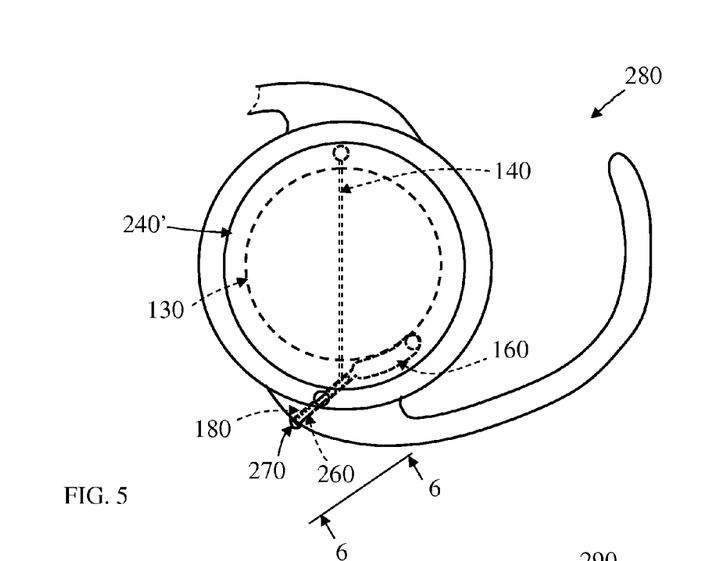
FIG. 5 illustrates a front view of the lens of the FIG. 4 with the blocking element placed into the blocking channel in its final position to block a fluid communication between the transparent and holding chambers. It shows the final multifocal multi-mode operating RDS lens assembly.

FIG. 5 demonstrates the final step of multi-mode operating multifocal RDS implant assembly according to the present invention. A special stamp sized to the diameter of the guiding surface and having the surface shape that faces towards the film 240 to be the mirror shape of the guiding surface shape is pressed against the elastic film thus forcing the elastic film 240' to take the shape of the guiding multifocal diffractive surface 130 and squeezing out the matching fluid from the transparent chamber into the holding chamber 160 via the channel 140 and the section of the blocking channel 180 between the channel 140 and holding chamber 160. The portion of the elastic film over the holding chamber 160 bulges as the additional matching fluid is pushed into the holding chamber cavity thus putting the corresponding portion of the elastic film over the holding chamber under tension. After the matching fluid is transferred into the holding chamber, the communication between the channel 140 of the transparent chamber and holding chamber 160 is blocked by pushing the blocking element 260 into the blocking chamber 180 further in until the blocking element head 270 comes in contact with the implant surface. The length of the blocking element 260 is such that it fills the section blocking channel 180 between the channel 140 and holding chamber 160 thus severing a fluid communication between the transparent chamber over the guiding surface 130 and holding chamber 160. The stamp then is removed from pressing the elastic film in. The result is implant 280 as the final multifocal multi-mode operating RDS lens. The outcome of the process is that the elastic film is maintained in the active state that confirms to the shape of the guiding diffractive surface 130 thus forming the multifocal multi-mode operating RDS lens in multifocal mode of operation with the optical multifocal performance defined by the guiding multifocal diffractive surface.

Figure 6:
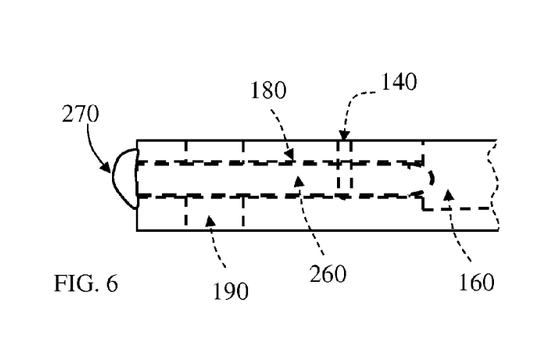
FIG. 6 illustrates a close-up taken from section 6-6 of FIG. 5 of the blocking mechanism in assembled form where the blocking element blocks a fluid communication between transparent and holding chambers.

FIG. 6 demonstrates a close-up of the blocking mechanism as a side view of the portion of the implant shown on FIG. 5. The blocking mechanism consists of blocking channel 180 with the cavity in a form of blocking through hole 190 crossing the blocking channel 180 with the section that connects the channel 140 and holding chamber 160. The blocking mechanism also includes blocking element 260 inserted into the blocking channel 180 to sever optical fluid communication between the channel 140 and holding chamber 160. The blocking element 260 includes blocking element head 270 to secure its position inside the blocking channel 180.

Figure 7:
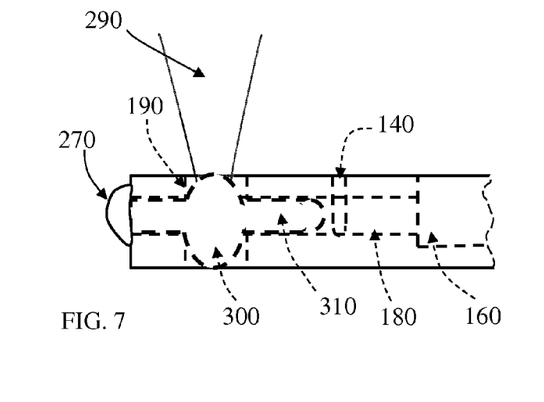
FIG. 7 is similar to FIG. 6 but now illustrates an unblocked blocking mechanism as a result of unblocking procedure by the laser beam irradiating the blocking element portion at the location of the blocking hole serving as a cavity of the blocking channel, where the corresponding blocking element portion fills the cavity as it takes a flowable form due to irradiation by the laser beam, and as the result of filling the cavity of the blocking hole, the length of the blocking element is reduced beyond the portion of the blocking chamber located between transparent and holding chambers thus opening the fluid communication between them.

FIG. 7 demonstrates blocking mechanism in unblocked state together with unblocking process of mode switching from one mode operation to another, in the case of the implant on FIG. 5 from multifocal to monofocal mode of operation. In accordance with present invention, the laser beam 290 is focused on the blocking element 260 within the blocking through hole 190. The blocking element material absorb laser radiation and melts within the blocking through hole 190 into flowable portion 300 that fills the space of the blocking through hole 190. The material volume increase at the flowable portion 300 is at the expanse of the blocking element portion internal to the location of the blocking through hole because wider blocking element head 270 does not allow the material feeding into flowable portion 300 at the exterior side of the blocking element, i.e. the blocking element head 270 prevents pulling the blocking element towards the blocking through hole 190 at the exterior side of the blocking element. The resulted blocking element 310 becomes short enough within the blocking channel 180 to be outside the segment connecting channel 140 and holding chamber 160. It opens fluid communication between the channel 140 and holding chamber 160 thus allowing to change the mode of operation of the implant. In more general term, a blocking through hole can be a cavity (aperture/hole/void) within the blocking channel characterized by an expanded space over the blocking channel for the blocking element to expand into with the blocking element portion within the cavity becoming a flowable material under the laser radiation.

The described above process of unblocking of the blocking mechanism is applied to the implant 280 in order to demonstrate the process but it is the general process to be applied to any type of multi-mode operating lens which includes transparent and holding chambers connected by the blocking mechanism to maintain the multi-mode operating lens in one mode of operation and converting to another mode of operation with remote unblocking the blocking mechanism. In the example of the implant 280, the excess of fluid flows into the transparent chamber from the holding chamber 160 to release the elastic film from active to resting states thus converting the implant from multifocal mode of operation into monofocal mode of operation.

The described above blocking mechanism and unblocking process allow a conversion of any single mode fluidic implant into multi-mode fluidic implant by introducing a holding chamber for managing a balance of fluid at the fluidic lens and placing the blocking channel for communicating the fluidic lens fluid of, so called transparent chamber, with the holding chamber. A blocking element placed into the blocking channel is to sever the fluid communication between the transparent chamber and holding chamber to freeze the lens in one mode operation and then unblocking fluid communication between transparent and holding chambers with the help of a laser beam to convert the fluidic lens in a different mode of operation now allowing fluid either flow to or from the holding chamber depending upon where the pressure is higher.

Figure 8:
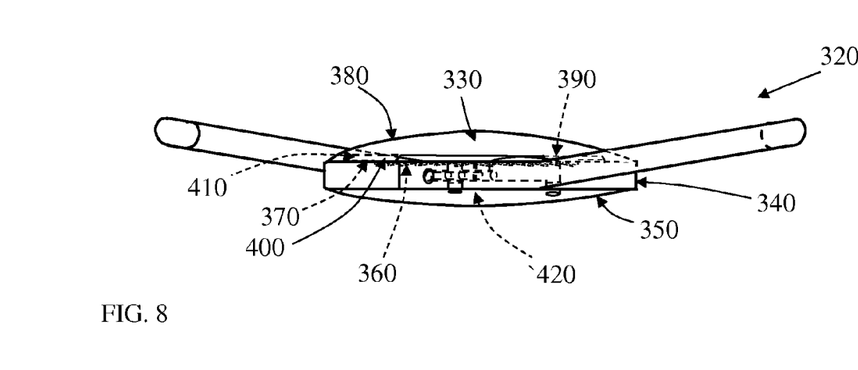
FIG. 8 demonstrates a side view of a two-piece multifocal multi-mode operating RDS lens with assembled blocking mechanism in multifocal mode of operation.

FIG. 8 demonstrates a side view of a two-piece multifocal multi-mode RDS lens 320 according to the present invention. The implant 320 consists of two parts—front optic body 330 and back optic body 340 with supporting members similar to a single piece lens such as 100 shown on the FIG. 2. The arrangement might be in reverse with haptic attached to front optic body or blocking mechanism together with an elastic film being at the front optic body. The back optic body 340 includes posterior surface 350 and front diffractive surface 360 within optical zone with largely flat base surface and the elastic film 370 adjacent to the diffractive surface ridges. The front optic body 330 includes anterior surface 380 and largely flat back surface 390. The front optic body 330 and back optic body 340 are connected to each other by connecting element 400, however it could be multiple connecting elements. The front optic body 330 and back optic body 340 are separated by the space, so called internal space 410. The internal space 410 allows the external to the diffractive surface 360 surface of the elastic film 370 to be in contact with the aqueous when the implant is placed in eye. The back optic body 340 can be made of a constant shape and far power of the implant 320 can be controlled by variable anterior surface 380 of the front optic body 330 to simplify the fabrication purpose. The blocking mechanism 420 similar to one described above in FIGS. 5 and 6 is located at the periphery of back optic body 340. The unblocking procedure is equivalent to one descried by the FIG. 7. The implant 320 is placed in the eye in multifocal mode of operation with the film 370 and implant in active state, i.e. conforming to diffractive multifocal surface 360. The unblocking procedure converts the film and implant in resting state for monofocal mode of operation. The material of the implant is transparent to the laser beam to allow for unblocking procedure. The diffractive multifocal surface might also be a refractive multifocal surface of multizone structure of zones of different powers for far and near foci.

Figure 9:
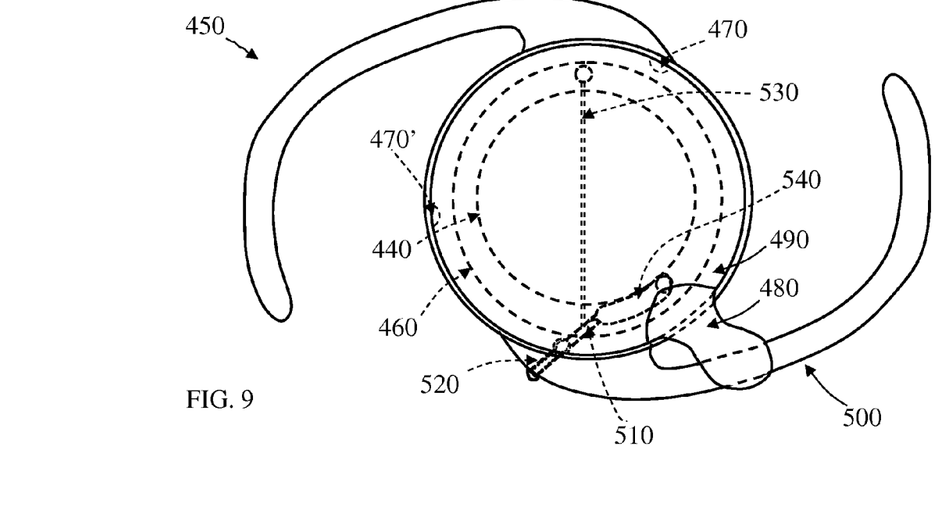

FIG. 9 demonstrates front view of an accommodating multi-mode operating RDS lens 450. The overall construction of the implant 450 can be equivalent to the implant 320 of FIG. 8, i.e. two-piece construction of front and back optic bodies with blocking mechanism placed at the back optic body together with the elastic film 460 adjacent to the guiding diffractive surface 440. In this case the diffractive surface 440 is to produce single focus imaging for near vision, i.e. kinoform for first order focus or optic for higher order focus. The diffractive surface may also include significant spherical aberration to provide intermediate focus. Thus, the guiding diffractive surface is a monofocal diffractive surface for near focus but it might also be a multifocal surface with near and intermediate foci. The guiding surface might also be refractive monofocal surface for near focus or for near intermediate foci. There are few other structural differences between accommodating implant 450 and multifocal implant 320 related to the fact that multifocal implant provides static imaging at multifocal or monofocal modes of operation but implant 450 provides dynamic imaging with alternating far and near foci in the accommodating mode of operation under the action of ciliary muscle of the eye. For this reason front and back optic bodies are attached to each other by spring elements 470 and 470', i.e. two elements in this case though it might be a different number, which are of flexible nature. In addition, there is activation member 480 attached to the front optic body 490 and close to the supporting member 480. The posterior (internal) surface of the front optic body 490 includes a post with a height that is close to the internal space width between front and back optic bodies. The post shape is similar to the shape of the holding chamber. It is shown that spring elements 470, 470' and activation member 480 are spaced by about 120 degrees. The surface of the post facing the back optic body is bonded to the exterior surface of the film at the area of the holding chamber 540.

As the blocking mechanism is in the blocking condition where the blocking element 510 placed into the blocking channel 520 to sever the fluid communication between the channel 530 and holding chamber 540 in order to maintain the implant 450 in the monofocal mode of operation where the elastic film 460 is in the relaxed state to produce refractive monofocal surface for far focus. The space between the film 460 and guiding surface 440 is filled with matching optical fluid to mask the guiding surface shape and to control the optical power of the implant 450 only by the film's external surface which is a monofocal refractive surface in the film resting state. Thus, the blocking mechanism in the blocking condition to fix the implant 450 in the corresponding monofocal mode of operation of a monofocal power for far vision.

Figure 10:
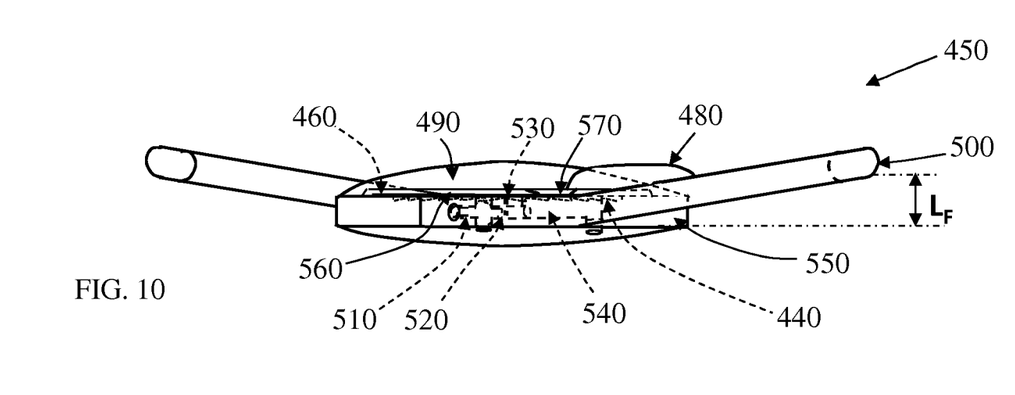
FIG. 10 demonstrates a side view of the accommodating multi-mode operating RDS lens for aphakia of the FIG. 9 in monofocal mode of operation which is equivalement to the configuration in the accommodating mode of operation with the elastic film being in resting state for far focus, i.e. optical fluid fills the transparent chamber with the external surface of the elastic film being in the resting state for far focus.
Figure 11:
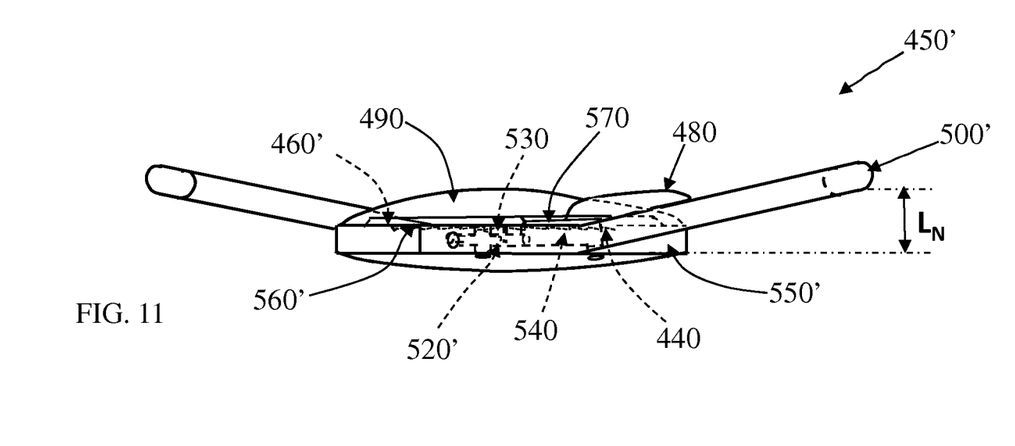
FIG. 11 demonstrates a side view of the accommodating multi-mode operating RDS lens for aphakia of the FIG. 9 in the accommodating mode of operation with the elastic film being in active state for near focus, i.e. fluid is pulled out from the transparent chamber for the film largely to take a shape of the diffractive guiding surface for near focus.

FIG. 10 shows side view of the implant 450 of the FIG. 9. It demonstrates front optic body 490 and back optic body 550 separated by internal space 560 and connected by spring elements shown on the FIG. 9. The elastic film 460 covers the guiding diffractive surface 440 and holding chamber 540 similar to the description on the FIG. 2 but in this case for the monofocal mode of operation. There is also post 570 protruded from the posterior surface of the front optic body 490 and bonded to the exterior surface of the film 460 at the location of the holding chamber 540. The blocking mechanism placed at the back optic body 550 includes blocking element 510 in the blocking channel 520 to sever fluid communication between the channels 530 and holding chamber 540 in order to maintain the film 460 in resting state for monofocal focus, i.e. the optical power of the implant is such that when added to the optical power of the eye the image of an object at far. The accommodating implant 450 is in the monofocal mode of operation as a monofocal refractive lens. In this condition the periphery of supporting member 500 is at the distance $L_F$ form the plane of the external edge of the back optic body 550. There is also activation element 480 attached to the anterior optic body 490 and being in contact with the supporting member 500 connected to the back optic body 550. The activation element 480 serves for mechanical interaction between front optic body 490 and back optic body 500 of the implant 450. It could be more than one activation elements connected to the front optic and each in contact with a supporting member or members. Instead of the activation element, a front optic body might be oversized as compared with the size of the back optic body in order to be in contact with a supporting member at the front optic periphery FIG. 11 demonstrates side view of the implant 450' after the implant 450 of FIG. 10 converted into accommodating mode of operation with unblocking the blocking mechanism as described at the FIG. 8. The fluid communication between the holding chamber 540 and channel 530 is open for the fluid to travel in and out of the transparent chamber. Under the action of eye ciliary muscle the angulation of the supporting member 500' bends into higher separation $L_N$ between the member 500' and the plane at he external edge of the back optic body 550'. The back optic body is designated with a different number from one on the FIG. 10 because the internal blocking mechanism now in the different unblocking configuration with shorten blocking element 520' with open fluid communication between the channel 530 and holding chamber 540. The activation element is fairly rigid member to avoid its bending with the haptic pressure. Thus, the supporting member 500' pushes the activation element 480 forward with ciliary muscle contraction, this in turn pushes the front optic body 490 forward thus increasing separation between front 490 and back 550' optic bodies. The spring members 470 of FIG. 9 help to maintain the front body position possibly very slightly tilting the front optic body 490 in relationship to back optic body 550'. The central aspect of the increase in the internal space 560' is that the post 570 lifts the film 460 at the location of the holding chamber thus increasing the volume of the holding chamber 540 to pull the optical fluid out of the transparent chamber between the film 460' and guiding surface 440. This in turn, forces the film 460' to take the shape of the guiding surface 440 to manifest equivalent optical power for near focus. Near focus means that a combination of optical powers of the implant 450' with optical power for near and eye's optical power results in the image of a near object. Thus, the accommodating implant 450' becomes diffractive monofocal lens with the power for near focus.

As the ciliary muscles are relaxed, the haptic takes the original shape of $L_F$ shown on the FIG. 10 to allow bringing the internal space 560 between front and back optic parts closer to each other releasing pressure at the holding chamber 540 by the post 570. The matching fluid flows back from the holding chamber to the space between the elastic film and the guiding diffractive surface (transparent chamber) thus switching the accommodating implant 450' back from the monofocal diffractive implant 450' for near focus into the monofocal refractive implant 450 for far focus.

It has been clinically documented the ability of posterior chamber lens with proper haptic configuration to move along the optical axis of the eye in the order of few tens of microns with ciliary muscle contraction and relaxation. This amount of the lens movement does not affect the ocular power of the eye as a whole but it is effective for accommodating RDS implant for switching between far and near foci because only small amount of matching fluid occupies the space between the elastic film and the guiding diffractive monofocal surface and its flow to the holding chamber requires about ten or so microns of internal space between front and back optic bodies increase to transfer the elastic film into the active state for near focus.

Thus, upon the implantation, the accommodating multi-mode operating RDS implant is in the monofocal mode of operation as a monofocal refractive lens for far vision. In a month or two, upon eye healing and establishing lens stabled and necessary position inside the capsular bag, the implant is remotely converted into accommodating mode of operation which allows the matching fluid transfers between resting and active states of the elastic film to provide far vision with ciliary muscles relaxation and near vision with the ciliary muscles contraction.

Similar to a posterior chamber monofocal lens lenses of equivalement haptics (supporting members) configuration, accommodating RDS implant in the monofocal mode of operation can also move as a whole along the optical axis in the order of about ten or more microns. Optical or ultrasound posterior chamber depth measurement allows testing for the implant's movement in its monofocal mode of operation and ultrasound microscopy allows observation of ciliary muscle contraction and relaxation in order to assess the movement in sync with the ciliary muscles actions before unblocking the fluid communication between the holding chamber and transparent chamber, i.e. converting the implant into accommodating mode of operation. This observation of the accommodating RDS implant movement offers addition indication of the likelihood of switching between far and near foci to be in sync with ciliary muscle contraction and relaxation upon unblocking procedure for the accommodating mode of operation.

The described above unblocking procedure can also be used for a phakic switchable optic introduced in the eye in a form of RDS corneal inlay or RDS phakic implant with operation between resting state for Far and active state for Near by communicating with the Sensor Cell for a direct interaction with the ciliary muscles of phakic presbyops. A description of the Sensor Cell is provided in the U.S. Pat. No. 8,608,600 and incorporated in this application. Additionally, a communication between the Sensor Cell and RDS implant can be provided by RF communication in general and by near field communication (NFC) in particular.

Multi-mode operation of an accommodating implant for the accommodating mode of operation where the first step is to install the implant in the monofocal mode of operation for far focus to allow testing for a potential issue and efficacy assessment before pursuing the second step of remote unblocking for the accommodating mode of operation, is the unique characteristic of the multi-mode operating implant. It allows either performing the second step, aborting it or conducting an adjustment of the implant before switching it to the accommodating mode of operation. Due to dynamic nature of an optical system for accommodation and likely differences between the patients, the multi-mode operation is necessary for matching the individual patient conditions with the expected performance for accommodation.

What is claimed is:
1. A switchable intraocular lens assembly configured for implantation in an eye, the assembly comprising:
    a) an optic body defining a body thickness between a first surface opposite a second surface, the optic body comprising:

i) at least two supporting members extending from a periphery of the optic body where the at least two supporting members are configured for implant fixation inside the eye;
ii) a guiding surface formed in the first surface;
iii) an elastic film disposed over the guiding surface forming a transparent chamber between the guiding surface and the elastic film;
iv) a holding chamber formed in the body thickness along the first surface and located outside a guiding surface periphery;
v) at least one fluid transport channel formed in the optic body fluidically connecting the transparent chamber and the holding chamber;
vi) a first hole disposed in the body thickness at one of the first and second surfaces, wherein the first hole is disposed outside the guiding surface periphery, and wherein the first hole is in fluidic communication with the at least one fluid transport channel;
vii) a second hole disposed in the body thickness at one of the first and second surfaces, the second hole in fluidic communication with the holding chamber;
viii) a blocking channel formed in the body thickness of the optic body, the blocking channel in fluidic communication with the at least one fluid transport channel and the holding chamber, the blocking channel having a blocking channel opening in the optic body at a proximal end of the blocking channel, where the holding chamber is connected at a distal end of the blocking channel, wherein the at least one fluid transport channel is connected to the blocking channel between the proximal and distal ends of the blocking channel;
ix) a cavity disposed at the body thickness through a portion of the blocking channel;
b) the elastic film disposed over the first hole, the second hole and the holding chamber; wherein the elastic film is sealed at or near the guiding surface periphery forming an enclosed cavity of the transparent chamber and wherein the elastic film is sealed at a periphery of the holding chamber forming an enclosed cavity of the holding chamber; and
c) a laser flowable blocking element having an enlarged head connected to an extension portion, where a length of the extension portion is more than a distance along the blocking channel from the blocking channel opening to the connection of the at least one fluid transport channel, wherein the extension portion of the laser flowable blocking element is disposed inside the blocking channel; and
d) an optical fluid disposed within the holding chamber.

2. The assembly of claim 1, wherein the guiding surface is a diffractive surface.

3. The assembly of claim 2, wherein the diffractive surface comprises a multifocal diffractive surface.

4. The assembly of claim 1, wherein the guiding surface is a refractive surface.

5. The assembly of claim 1, wherein the optical fluid has a similar index of refraction in comparison to the optic body.

6. The assembly of claim 1, wherein in a first state the elastic film disposed over the guiding surface conformably matches the shape of the guiding surface, and wherein the extension portion of the laser flowable blocking element is severing fluidic communication between the holding chamber and the at least one fluid transport channel, and wherein the optical fluid in the holding chamber has a greater pressure in comparison to the transparent chamber.

7. The assembly of claim 6, wherein in a second state the elastic film disposed over the guiding surface does not conformably match the shape of the guiding surface and forms a refractive surface, and wherein the extension portion of the laser flowable blocking element is not severing fluidic communication between the holding chamber and the at least fluid transport channel, and wherein the optical fluid in the holding chamber has an equalized pressure in comparison to the transparent chamber.

8. The assembly of claim 7, wherein in the first state the intraocular lens assembly comprises a multifocal mode of operation and in the second state the intraocular lens assembly comprises a monofocal mode of operation.

9. The assembly of claim 7, wherein in the first state the intraocular lens assembly comprises a monofocal mode of operation and in the second state the intraocular lens assembly comprises an accommodating mode of operation.

10. The assembly of claim 9, wherein the monofocal mode of operation is either far or near foci and the accommodating mode of operation is the other of the far or near foci.

11. The assembly of claim 1, wherein the laser flowable blocking element comprises polypropylene.

12. The assembly of claim 1, wherein the laser flowable blocking element is configured to melt into a flowable state under a laser radiation, wherein in a first state before laser radiation the blocking element severs fluidic communication between the at least one fluid transport channel and holding chamber, and wherein in a second state after laser radiation the blocking element has receded into the cavity and opened fluidic communication between the at least one fluid transport channel and the holding chamber.

13. The assembly of claim 1, wherein a width of the enlarged head of the blocking element is bigger than a blocking channel opening width.

14. A switchable intraocular lens assembly configured for implantation in an eye, the assembly comprising:
a) an optic body defining a body thickness between a first surface opposite a second surface, the optic body comprising:
i) at least two supporting members extending from a periphery of the optic body where the at least two supporting members are configured for implant fixation inside the eye;
ii) a guiding surface formed in the first surface;
b) an elastic film disposed over the guiding surface, wherein the elastic film is sealed at or near a guiding surface periphery forming a transparent chamber between the guiding surface and the elastic film;
c) a holding chamber formed in the body thickness located outside the guiding surface periphery;
d) a blocking channel formed in the body thickness of the optic body, the blocking channel in fluidic communication between the transparent chamber and the holding chamber, the blocking channel having a blocking channel opening in the optic body at a proximal end of the blocking channel, where the holding chamber is connected at a distal end of the blocking channel;
e) a laser accessible cavity formed in the optic body and disposed through a portion of the blocking channel between the blocking channel opening and the fluidic connection to the guiding surface;
f) a laser flowable blocking element disposed at least partially inside the blocking channel, the laser flowable blocking element configured to melt into a flowable state under a laser radiation; and g) an optical fluid disposed within the holding chamber under a pressure greater or lesser in comparison to a pressure in the transparent chamber.

15. The assembly of claim 14, wherein in a first state the elastic film disposed over the guiding surface conformably matches the shape of the guiding surface, and wherein the portion of the laser flowable blocking element is severing fluidic communication between the holding chamber and the transparent chamber.

16. The assembly of claim 15, wherein in a second state the elastic film disposed over the guiding surface does not conformably match the shape of the guiding surface and forms a refractive lens, and wherein the extension portion of the laser flowable blocking element is not severing fluidic communication between the holding chamber and the transparent chamber, and wherein the optical fluid in the holding chamber has an equalized pressure in comparison to the transparent chamber.

17. The assembly of claim 16, wherein in the first state the intraocular lens assembly comprises a multifocal mode of operation and in the second state the intraocular lens assembly comprises a monofocal mode of operation.

18. The assembly of claim 16, wherein in the first state the intraocular lens assembly comprises a monofocal mode of operation and in the second state the intraocular lens assembly comprises an accommodating mode of operation.

19. An intraocular lens assembly, comprising:
a) an optic body defining a body thickness between a first surface opposite a second surface, the optic body including at least two supporting members extending from a periphery of the optic body where the at least two supporting members are configured for implant fixation inside an eye, the optic body comprising:
  i) a blocking channel formed in the body thickness of the optic body between the first and second surfaces extending from a proximal end to a distal end, the blocking channel having a blocking channel opening in the optic body at the proximal end of the blocking channel;
  ii) a cavity disposed through the body thickness at the first surface and disposed through a portion of the blocking channel; and
b) a laser flowable blocking element having an enlarged head connected to an extension portion, where a length of the extension portion is more than a distance along the blocking channel from the blocking channel opening to the cavity, wherein the extension portion of the laser flowable blocking element is disposed inside the blocking channel.

20. The assembly of claim 19, wherein the laser flowable blocking element comprises polypropylene.

21. The assembly of claim 19, wherein the laser flowable blocking element is configured to melt into a flowable state under a laser radiation focused within the cavity, wherein in a first state before laser radiation the extension portion has a first length, and wherein in a second state after laser radiation the extension portion has a shorter length in comparison to the first length as a portion of the extension portion has receded into the cavity.

22. The assembly of claim 19, wherein a width of the enlarged head of the blocking element is bigger than a blocking channel opening width.

23. An intraocular lens, comprising:
an optic body defining a body thickness between a first surface opposite a second surface;
at least two supporting members extending from a periphery of the optic body where the at least two supporting members are configured for implant fixation inside an eye;
an elastic film attached to the optic body, the elastic film forming a transparent chamber configured to focus an object with the intraocular lens placement inside the eye;
a holding chamber formed in the body thickness and located outside a transparent chamber periphery;
a blocking channel formed in the body thickness of the optic body providing fluidic communication between the transparent chamber and the holding chamber;
a cavity disposed in the body thickness through a portion of the blocking channel;
a laser flowable blocking element disposed in the blocking chamber to sever fluid communication between the transparent chamber and the holding chamber; and
an optical fluid disposed within the holding chamber under a pressure greater or lesser in comparison to a pressure in the transparent chamber;
wherein the laser flowable blocking element is configured to melt into a flowable state under a laser radiation, wherein in a first state before laser radiation the blocking element severs fluidic communication between transparent chamber and holding chamber, and wherein in a second state after laser radiation the blocking element has receded into the cavity and opened fluidic communication between the transparent chamber and the holding chamber.

24. The lens of claim 23, wherein the optical fluid has a similar index of refraction in comparison to the optic body.

25. The lens of claim 23, wherein the laser flowable blocking element comprises polypropylene.

26. The assembly of claim 14, wherein the laser flowable blocking element includes a blocking element head disposed adjacent the blocking channel opening, wherein the blocking element head is larger than the blocking channel opening.

* * * * *